United States Patent [19]

Cacheris et al.

[11] Patent Number: 5,560,902
[45] Date of Patent: Oct. 1, 1996

[54] MICROFLUIDIZATION OF RADIOACTIVE CALCIUM/OXYANION-CONTAINING PARTICLES

[75] Inventors: William P. Cacheris, Florissant; Linda Meeh, St. Louis, both of Mo.

[73] Assignee: Mallinckrodt Medical, Inc., St. Louis, Mo.

[21] Appl. No.: 419,800

[22] Filed: Apr. 11, 1995

Related U.S. Application Data

[62] Division of Ser. No. 249,776, Jul. 26, 1994, Pat. No. 5,419,892, which is a division of Ser. No. 38,329, Mar. 29, 1993, Pat. No. 5,342,609, which is a continuation-in-part of Ser. No. 948,540, Sep. 22, 1992, Pat. No. 5,344,640, which is a continuation-in-part of Ser. No. 784,325, Oct. 22, 1991, abandoned.

[51] Int. Cl.$^6$ .................................................. A61K 51/00
[52] U.S. Cl. .................... 424/1.29; 424/602; 424/639; 424/643; 424/648; 424/646; 423/700; 128/653.4
[58] Field of Search .............................. 424/9.42, 602, 424/639, 643, 648, 646, 9.4, 1.29; 423/700; 128/653.4, 654

[56] References Cited

U.S. PATENT DOCUMENTS

| | | | |
|---|---|---|---|
| 5,342,609 | 8/1994 | Meeh et al. | 424/9.32 |
| 5,344,640 | 9/1994 | Deutsch et al. | 424/9.32 |
| 5,419,892 | 5/1995 | Cacheris et al. | 424/9.42 |

*Primary Examiner*—Gary E. Hollinden
*Attorney, Agent, or Firm*—Brian K. Stierwalt

[57] ABSTRACT

Methods of preparing solid apatite particles using a microfluidizer, for use in medical diagnostic imaging such as magnetic resonance imaging, X-ray, and ultrasound. The desired apatite particles are synthesized, passed through a microfluidizer, and purified to remove excess base, salts, and other materials used to synthesize the particles. The microfluidizer causes two high pressure streams to interact at ultra high velocities in a precisely defined microchannel. Microfluidization of preparations causes small (<5 μm) and uniform particles to be formed. Coating and purifying (especially by tangential flow filtration) the particles improves particle stability.

20 Claims, 2 Drawing Sheets

MICROFLUIDIZATION OF RADIOACTIVE CALCIUM/OXYANION-CONTAINING PARTICLES

CROSS REFERENCE TO RELATED APPLICATIONS

This is a divisional of application Ser. No. 08/249,776 filed on Jul. 26, 1994; now U.S. Pat. No. 5,419,892 which is a divisional application of U.S. Ser. No. 08/038,329 filed on Mar. 29, 1993 issued as U.S. Pat. No. 5,342,609; which is a Continuation-In-Part application of U.S. Ser. No. 07/948,540 filed on Sep. 22, 1992 issued as U.S. Pat. No. 5,344,640; which is a Continuation-In-Part application of U.S. Ser. No. 07/784,325 filed on Oct. 22, 1991 now abandoned.

BACKGROUND OF THE INVENTION

This invention relates to the preparation of calcium/oxyanion-containing particles for use in medical diagnostic imaging, such as magnetic resonance imaging ("MRI"), ultrasound, and X-ray. In particular, the present invention is directed to the use of a microfluidizer for the preparation of calcium/oxyanion-containing particles having a uniform small (<5 μm) size distribution. The present invention also includes the use of tangential flow filtration for particle purification.

The use of contrast agents in diagnostic medicine is rapidly growing. In X-ray diagnostics, for example, increased contrast of internal organs, such as the kidneys, the urinary tract, the digestive tract, the vascular system of the heart (angiography), etc., is obtained by administering a contrast agent which is substantially radiopaque. In conventional proton MRI diagnostics, increased contrast of internal organs and tissues may be obtained by administering compositions containing paramagnetic metal species which increase the relaxivity of surrounding protons. In ultrasound diagnostics, improved contrast is obtained by administering compositions having acoustic impedances different than that of blood and other tissues.

Often it is desirable to image or treat a specific organ or tissue. Effective organ- or tissue-specific diagnostic agents accumulate in the organ or tissue of interest. Copending patent application Ser. No. 07/948,540, filed Sep. 22, 1992, titled "Treated Apatite Particles for Medical Diagnostic Imaging," which is incorporated herein by reference, discloses the preparation and use of apatite particles for medical diagnostic imaging. This patent application also describes methods for preparing apatite particles which provide organ- or tissue-specific contrast. By carefully controlling the particle size and route of administration, organ specific imaging of the liver, spleen, gastrointestinal tract, or blood pool is obtained.

In general, the apatite particles are prepared by modifying conventional methods for preparing hydroxyapatite (sometimes referred to as "hydroxylapatite"). For example, stoichiometric hydroxyapatite, $Ca_{10}(OH)_2(PO_4)_6$, is prepared by adding an ammonium phosphate solution to a solution of calcium/ammonium hydroxide. Useful apatite particles may also be prepared by replacing calcium with paramagnetic metal ions. Other apatite derivatives are prepared by replacing the $OH^-$ with simple anions, including $F^-$, $Br^-$, $I^-$, or $½[CO_3^{2-}]$.

Various techniques for controlling the particle size for certain calcium phosphate-containing compounds (apatites) are disclosed in copending application Ser. No. 07/948,540. For example, slower addition rates (introduction of the precipitating anion or cation), faster stirring, higher reaction temperatures, and lower concentrations generally result in smaller particles. In addition, sonication during precipitation, turbulent flow or impingement mixers, homogenization, and pH modification may be used to control particle size. Other means, such as computer controlled autoburets, peristaltic pumps, and syringes, may be used to control the release of precipitating ions to produce smaller particles.

Due to the small size and nature of apatite particles, they tend to aggregate. Particle aggregation may be inhibited by coating the particles with coating agents, while agglomerated particles may be disrupted by mechanical or chemical means and then coated with a coating agent having an affinity for the apatite.

One preferred method of obtaining small, uniformly sized, manganese-doped apatite particles is to dropwise add a degassed solution of $(NH_4)_2HPO_4$ and $NH_4OH$ into a rapidly stirring degassed solution of Ca $(NO_3)_2 \cdot 4H_2O$ and Mn $(NO_3)_2 \cdot 6H_2O$. The resulting apatite particles are then reacted with a solution of 1-hydroxyethane-1,1-diphosphonic acid (HEDP). The smaller particles are separated from larger particles by repeated centrifuging and collection of the supernatant. The particles are then washed to remove base and salts by centrifuging at a higher rpm, discarding the supernatant, resuspending the solid pellet in water, and recentrifuging.

Although the foregoing procedure produces small-sized apatite particles having good size distribution and good medical diagnostic imaging properties, the repeated centrifuging, decanting, and washing causes the process to be tedious and time-consuming. It, therefore, would be a significant advancement in the art to provide an improved method for rapidly preparing calcium/oxyanion-containing particles for medical diagnostic applications having a controlled particle size distribution and good yield.

Such methods for preparing calcium/oxyanion-containing particles are disclosed and claimed herein.

SUMMARY OF THE INVENTION

The present invention provides methods of preparing calcium/oxyanion-containing particles, including apatites and apatite precursors, using a microfluidizer. The particles thus prepared, are for use in medical diagnostic imaging, such as magnetic resonance imaging, X-ray, and ultrasound applications. The desired calcium/oxyanion-containing particles are synthesized, passed through a microfluidizer, and purified to remove excess base, salts, and other materials used to synthesize the particles. The microfluidizer causes two high pressure streams to interact at ultra high velocities in a precisely defined microchannel. Use of the microfluidizer results in significant reduction in the average particle size. Purifying the particles, preferably using tangential flow filtration, as well as coating the particles, improves particle stability.

DETAILED DESCRIPTION OF THE INVENTION

Figure 1:
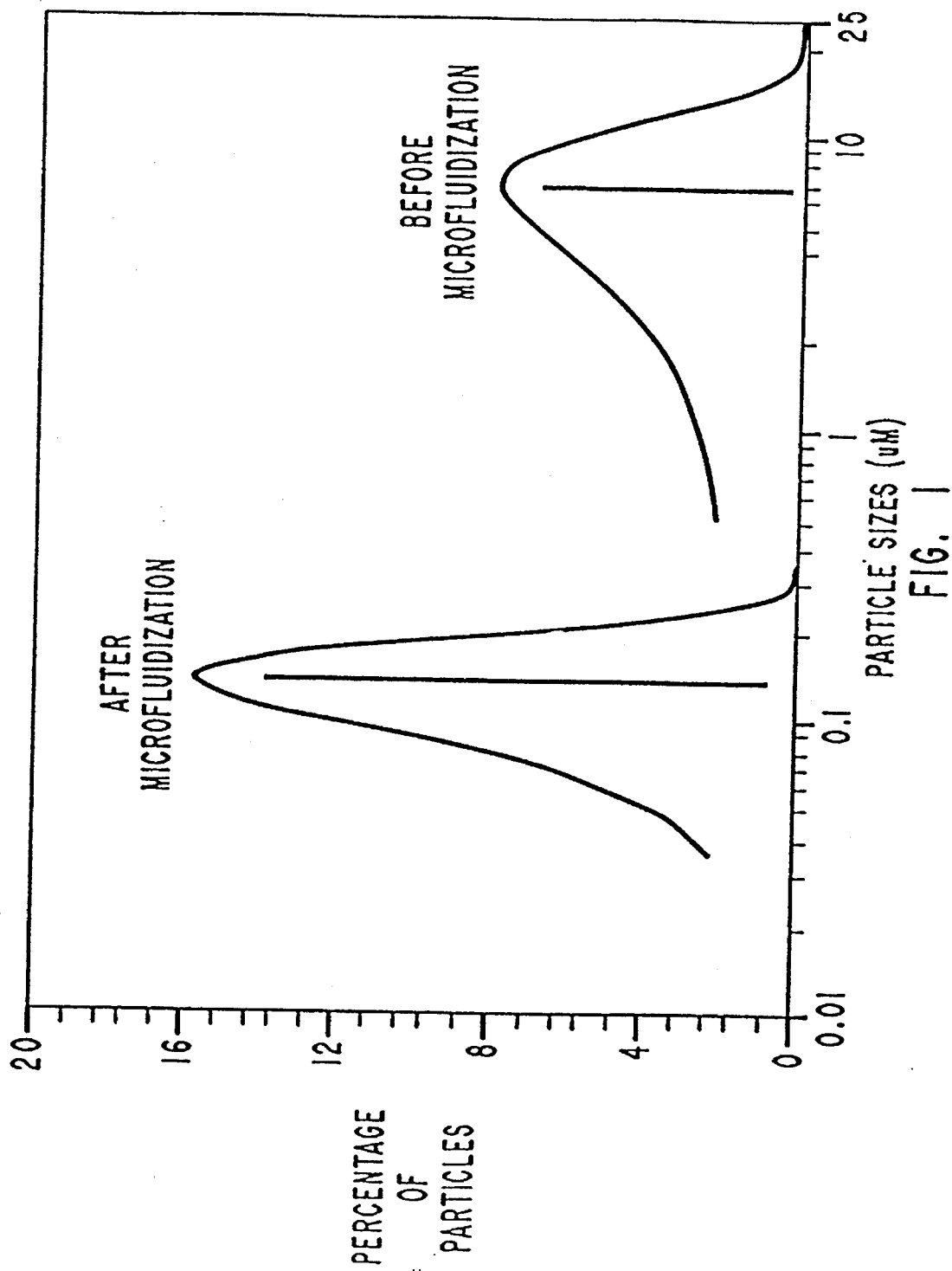
FIG. 1 is a graphical representation of the particle size distribution of manganese-doped hydroxyapatite particles prepared according to Example 8, before and after passing through a microfluidizer.

The present, invention provides methods for preparing calcium/oxyanion-containing particles, including apatites and apatite precursors, especially hydroxyapatite, having uniform, small (<5 μm) particle size and uniform distribution through use of a microfluidizer.

As used herein, calcium/oxyanion-containing particles include calcium phosphate minerals, apatites, and apatite precursors of the general formula $Ca_nM_mX_rY_s$, where M is a paramagnetic metal ion, radiopaque metal ion, radioactive metal ion, or stoichiometric mixture of metal ions, X is a simple anion, Y is an oxyanion including tetrahedral oxyanions, protonated or unprotonated, carbonate, or mixtures thereof, m is from 0 to 10, n is from 1 to 10, s is >1, and r is adjusted as needed to provide charge neutrality.

As used herein, apatite precursors include compounds within the scope of the above general formula having one or more amorphous phases which, when sintered, may become crystalline apatites.

Possible paramagnetic metal ions which can be used in the calcium/oxyanion-containing particles of the present invention include: chromium(III), manganese(II), iron(II), iron(III), praseodymium(III), neodymium(III), samarium(III), ytterbium(III), gadolinium(III), terbium(III), dysprosium(III), holmium(III), erbium(III), or mixtures thereof with each other or with alkali or alkaline earth metals.

Certain radiopaque heavy metals, such as bismuth, tungsten, tantalum, hafnium, lanthanum and the lanthanides, barium, molybdemnn, niobium, zirconium, and strontium may also be incorporated into particles to provide X-ray contrast.

Typical simple anions which can be used in the calcium/oxyanion-containing particles of the present invention include: $OH^-$, $F^-$, $Br^-$ $I^-$, $1/2[CO_3^{2-}]$, or mixtures thereof. The tetrahedral oxyanions used in the present invention may optionally include radiopaque metals or radioactive metals. Suitable tetrahedral oxyanions are nonoxidizing and stable to hydrolysis. Examples of suitable tetrahedral oxyanions for use in the present invention include: $PO_4^{3-}$, $AsO_4^{3-}$, $WO_4^{2-}$, $MoO_4^{2-}$, $VO_4^{3-}$, $Sio_4^{4-}$, and $GeO_4^{4-}$, and when stable protonated forms of these. Phosphate is a currently preferred tetrahedral oxyanion.

By controlling the particle size, organ specific imaging or therapy of the liver or gastrointestinal tract is obtained. When apatite particles having a size in the range from about 5 nm to about 5 μm are injected into the vascular system, the particles collect in the liver or spleen (the RES system) because a normal function of these organs is to purify the blood of foreign particles. Once the particles have collected in the liver or spleen, these organs may be imaged by the desired medical diagnostic imaging technique.

Depending on the diagnostic imaging technique, calcium/oxyanion containing particles are treated to be paramagnetic, radiopaque, or echogenic. For example, paramagnetic metal species may be incorporated into the particles to improve magnetic resonance contrast, and radiopaque species may be incorporated to provide X-ray contrast. Particle density, and corresponding echogenic characteristics, can be controlled to impart low or high acoustic impedance relative to blood. The calcium/oxyanion-containing particles may also be fluorinated to form stable, nontoxic compositions useful for $^{19}F$ imaging. The presence of a paramagnetic metal species in these particles may reduce $^{19}F$ and proton relaxivity, thereby enhancing MRI, MRS, or MRSI.

Hydroxyapatite doped with a paramagnetic metal can be prepared by mixing a basic (pH 10–12) phosphate solution with a calcium/paramagnetic metal solution at native pH. It has been found that the paramagnetic ions incorporated into the apatite particle tend to oxidize during particle synthesis. To prevent metal oxidation the amount of oxygen in the aqueous reactant solutions is minimized. Oxygen minimization is obtained by synthesis at high temperature, such as 100° C. or by degassing the aqueous reactant solutions with an inert gas such as argon, nitrogen, or helium.

Antioxidants, such as gentisic acid and ascorbic acid, added during or after apatite particle synthesis may also be used to prevent metal ion oxidation. Reducing agents, such as $NaBH_4$, have been found to reduce metal ions that are unintentionally oxidized during apatite particle synthesis.

Paramagnetic particles may also be prepared by adsorbing paramagnetic metal ions onto the particle. For example, manganese can be adsorbed to hydroxyapatite particles by taking a slurry of hydroxyapatite and adding $Mn(NO_3)_2$ with stirring. Applying energy, such as ultrasonic power or heat, to the resulting mixture may also facilitate the reaction. The resulting mixture can be separated by either centrifugation and decantation or by filtration. Any excess manganese may be removed by washing with large amounts of water. The manganese adsorbed particles can then be stabilized against oxidation and particle agglomeration with a suitable coating agent. The same procedure may be used with other paramagnetic cations. The amount of manganese adsorbed onto the particle surface, as a percentage of the total calcium in the particle, is in the range from about 0.1% to about 50%. Such particles exhibit very high relaxivities and rapid liver enhancement in magnetic resonance imaging studies.

Particle Size Reduction and Production of Particles of Uniform Size using a Microfluidizer It has been found that passing calcium/oxyanion-containing particles, including apatites and apatite precursors, through a microfluidizer results in dramatic particle size reduction. A microfluidizer, such as those produced by Microfluidics Corporation, Newton, Mass., causes two high pressure fluid streams to interact at ultra high velocity. It is postulated that shear, impact and cavitation forces act on the fluid streams to achieve submicron particle reduction with uniform distribution. Fluid pressures typically range from 2000 psi to 30,000 psi with some production size microfluidizers capable of handling pressures up to 40,000 psi.

Experimental results suggest that particle size reduction using a microfluidizer can be obtained from apatite particles regardless of whether the particles are first stabilized with a coating agent or purified from the base, salts, and other compounds used to prepare the particles. The particles may be purified or unpurified, coated or uncoated when passed through the microfluidizer. However, it appears that the microfluidized apatite particles show better stability with removal of the base, salts, and other compounds in the reaction mixture. The particles tend to become larger when stored in the basic reaction solution, but growth of purified particles is either stopped or inhibited by purification of the particles from the mixture. Particle purification can be obtained by processes such as repeated centrifuging and decanting, passing through a desalting column, and filtration, preferably tangential flow filtration or ultrafiltration.

Particle Coating

Stabilized calcium/oxyanion-containing particles, including apatites and apatite precursors, are desirable for in vivo use as medical diagnostic imaging agents. Such particles tend to aggregate. Although the reasons calcium/oxyanion-containing particles aggregate is not fully understood, it has been found that several different coating agents are able to inhibit particle aggregation. For example, these particles may be stabilized by treatment with coating agents such as di- and polyphosphonate-containing compounds or their salts, such as 1-hydroxyethane-1,1-diphosphonate (HEDP), pyrophosphate, aminophosphonates; carboxylates and polycarboxylate-containing compounds such as oxalates and citrates; alcohols and polyalcohol-containing compounds; compounds containing one or more phosphate, sulfate, or sulfonate moiety; and biomolecules such as peptides, proteins, antibodies, and lipids all have been shown to inhibit particle aggregation. Such coating agents stabilize the small particles by reducing further particle growth and promoting particle suspension.

When used in magnetic resonance imaging, particle relaxivity is enhanced by allowing more water accessible to the particle surface. By limiting particle size and increasing the available surface area, relaxivity may be improved.

In addition to the coating agents identified above, conventional particle coating techniques may also be used in the manufacturing processes of the present invention. Typical coating techniques are identified in International Publication Numbers WO 85/02772, WO 91/02811, and European Publication Number EP 0343934, which are incorporated by reference.

For instance, agglomerated particles may be disrupted by mechanical or chemical means and then coated with polymers such as carbohydrates, proteins, and synthetic polymers. Dextran having a molecular weight in the range from about 10,000 to about 40,000 is one currently preferred coating material. Albumin and surfactants, such as tween 80, have also been used to reduce particle aggregation. One common characteristic of useful apatite coating agents is their ability to modify the particle surface charge, or zeta potential.

It will be appreciated that the calcium phosphate-containing particles within the scope of the present invention may be coated before, during, or after passage through the microfluidizer. When coated during passage through the microfluidizer, one fluid stream is the coating agent, while the other fluid stream is the particulate stream.

The currently preferred mechanical means for reducing particle size is microfluidization, but other means such as heating, sonication, other forms of particle energization, such as irradiation, and chemical means, such as pH modification or combinations of these types of treatment, such as pH modification combined with sonication may be used.

Diagnostic Pharmaceutical Formulations

The calcium/oxyanion-containing particles of this invention may be formulated into diagnostic compositions for parenteral administration. For example, parenteral formulations advantageously contain a sterile aqueous solution or suspension of treated apatite or apatite precursor particles according to this invention. Various techniques for preparing suitable pharmaceutical solutions and suspensions are known in the art. Such solutions also may contain pharmaceutically acceptable buffers and, optionally, electrolytes such as sodium chloride. Parenteral compositions may be injected directly or mixed with a large volume parenteral composition for systemic administration.

The diagnostic compositions of this invention are used in a conventional manner in medical diagnostic imaging procedures such as magnetic resonance, X-ray, and ultra-sound imaging. The diagnostic compositions are administered in a sufficient amount to provide adequate visualization, to a warm-blooded animal either systemically or locally to an organ or tissues to be imaged, then the animal is subjected to the medical diagnostic procedure. Such doses may vary widely, depending upon the diagnostic technique employed as well as the organ to be imaged.

The following examples are offered to further illustrate the present invention. These examples are intended to be purely exemplary and should not be viewed as a limitation on any claimed embodiment.

EXAMPLE 1

Preparation of Hydroxyapatite Particles Doped with Mn, Treated with HEDP, Purified and Passed through Microfluidizer Manganese containing hydroxyapatite particles were prepared by the following general procedure. A procedure is described for particles containing 10% Mn (compared to the total metal content) but other percentages are also applicable.

Into a 1 L erlenmeyer flask were placed 10.5 g of $(NH_4)_2HPO_4$, 100 mL of concentrated $NH_4OH$ and 350 mL of D.I. water. The mixture was stirred for two hours with a continuous heavy argon flow (degassing). In a separate 1 L erlenmeyer flask were placed 28.9 g of $Ca(NO_3)_2 \cdot 4H_2O$ and 2.4 g of $Mn(NO_3)_2 \cdot 6H_2O$ 400 mL of D.I. water. The metal nitrate solution was degassed with argon for 2 hours. The phosphate solution was then added dropwise to the rapidly stirred metal nitrate mixture over two hours with a peristaltic pump. A continuous argon flow was maintained throughout the course of the reaction. The reaction mixture was stirred for an additional two hours after the addition was complete. A solution of 8.3 mL of a 60% solution HEDP (acid form) in 25 mL of D.I. water was degassed for 30 minutes then added in one aliquot to the hydroxyapatite mixture. The resulting slurry was stirred for 15 minutes.

The entire reaction mixture was centrifuged at one time at 2400 rpm for 15 minutes. The supernatant was discarded and the solid residue in each tube resuspended in water. The slurry was re-centrifuged at 2400 rpm and the milky supernatant was collected. The solid was resuspended twice more and centrifuged at 2400 rpm. The three washes were combined and centrifuged at 7000 rpm for 30 minutes. The resulting solid pellet was separated from the supernatant by decantation, and the pellet was washed (D.I. $H_2O$) and centrifuged three times, and the supernatants were discarded. After washing, the solid pellet was suspended in 30 mL of D.I. $H_2O$.

The preparation was stored at room temperature for one month. The particle size was analyzed and found to be 280 nm (2.9 chi squared, 0.31 coefficient of variance). The particulate suspension was passed through a microfluidizer at approximately 5000 psi. After one pass through the microfluidizer, the particle size was reduced to 125 nm (0.43 chi squared, 0.35 coefficient of variance). After another pass through the microfluidizer at a pressure of approximately 10,000 psi, the size did not change significantly, 144 nm (0.20 chi squared, 0.28 coefficient of variance). At three hours and 36 hours after passing through the microfluidizer, the particle size remained essentially constant at 159 nm and 148 nm, respectively.

EXAMPLE 2

Preparation of Hydroxyapatite Particles Doped with Mn and Treated with HEDP and Passed through Microfluidizer Unpurified Manganese containing hydroxyapatite particles were prepared according to the procedure of Example 1, except that the particles were not purified by centrifuging, decanting, and washing, but left in the base and salt solution. The particulate suspension (average size >1 μm, chi squared >201) was passed through a microfluidizer at approximately 5000 psi. After one pass through the microfluidizer, the particle size was 87 nm (2.3 chi squared, 0.41 coefficient of variance). After five passes through the microfluidizer at pressures from 5000 psi to 7000 psi, the particle size was 89 nm (0.88 chi squared, 0.37 coefficient of variance).

The resulting particles were too small to pellet at 2400 rpm and were left in the base and salts. There was no indication that multiple passes through the microfluidizer made smaller particles, but it appears the uniformity was increased. Twenty hours after passing through the microfluidizer the particle size has increased to 713 nm (21.1 chi squared, 0.53 coefficient of variance). Although the chi squared was large, indicating a poor fit to a gaussian distribution, the coefficient of variance was small with 99% of the particles less than 2 μm and 75% less than 825 nm. The relaxivity ($R_1$) of these particles 2 hours after formation was approximately 22 $mM^{-1}s^{-1}$.

EXAMPLE 3

Preparation of Hydroxyapatite Particles Doped with Mn and Passed through Microfluidizer Unpurified with a simultaneous coaxial stream of HEDP Manganese containing hydroxyapatite particles were prepared according to the procedure of Example 1, except that the particles were not coated with HEDP and were not purified by centrifuging, decanting, and washing, but left in the base and salt solution. The particulate suspension was passed as one stream into a microfluidizer. The other microfluidizer stream consisted of a HEDP solution prepared according to the procedure of Example 1. The two streams passed through the microfluidizer at a pressure of 10,000 psi. The resulting particulate suspension had a particle size of 70 nm (2.4 chi squared, 0.42 coefficient of variance). The particles were not purified from base and salts. Two hours after formation the particle size was 87 nm (1.8 chi squared, 0.41 coefficient of variance). Thirty-six hours after formation the particle size was 903 nm (0.84 chi squared, 0.45 coefficient of variance) indicating the particles had grown uniformly to a large size. The relaxivity ($R_1$) of these particles was 24 $mM^{-1}s^{-1}$.

EXAMPLE 4

Preparation of Hydroxyapatite Particles Doped with Mn and Passed through Microfluidizer Unpurified into Neutral HEDP Solution Manganese containing hydroxyapatite particles were prepared according to the procedure of Example 1, except that the particles were not coated with HEDP and were not purified by centrifuging, decanting, and washing, but left in the base and salt solution. The particulate suspension was passed through a microfluidizer at 10,000 psi and into a beaker of neutral HEDP. The neutral HEDP solution was prepared from 8.3 mL of a 60% solution HEDP (neutral form) in 25 mL of D.I. water.

The resulting particulate solution had an average particle size of 1333 nm (7.3 chi squared, 0.40 coefficient of variance). Two hours after formation, the particle size was 884 nm (8.3 chi squared, 0.46 coefficient of variance). The results suggest that the use of acidic HEDP is useful in the formation of small particles and the neutral form of HEDP may be used when larger particles are desired.

Examples 1–4 indicate that the particle size of manganese doped hydroxyapatite may be substantially reduced by the shear, impact and cavitation forces present within the microfluidizer.

EXAMPLE 5

Preparation of Hydroxyapatite Particles Doped with Mn, Washed, Coated with Aminotri(methylene Phosphonic acid) (ATMP), and Passed through Microfluidizer Manganese containing hydroxyapatite particles were prepared according to the procedure of Example 1, except that the particles were not coated with HEDP and the particles were washed free of base and salts by centrifuging three times at 2400 rpm. Degassed water was used to wash the pelleted particles following centrifuging. An ATMP solution was prepared by mixing 0.0027 moles or 1.6 mL of a 50% aqueous solution with 25 mL D.I. $H_2O$ and degassing for 30 minutes under argon. The ATMP solution was added dropwise to the washed particles resulting in a "white" slurry. The slurry was passed through a microfluidizer at 10,000 psi. After passing through the microfluidizer, the particles had an estimated size of 84 nm (1.3 chi squared, 0.52 coefficient of variance). There was some oxidation of manganese with time as evident from a brown appearance in the particles. After six days there were two populations of particles, 46 nm and >2 μm. The percentages of each component could not be determined due to the limits of the particle analyzer and settling of the larger particles.

EXAMPLE 6

Preparation of Hydroxyapatite Particles Doped with Mn, Coated with HEDP, Passed through Microfluidizer, and Purified Manganese containing hydroxyapatite particles were prepared according to the procedure of Example 1, except that the particles were not coated with HEDP and were not purified by centrifuging, decanting, and washing, but left in the base and salt solution. An HEDP solution prepared according to the procedure of Example 1 was added dropwise to the particles. The particle size before passing through a microfluidizer was 1498 nm (13.4 chi squared, 0.93 coefficient of variance). After passing the particulate suspension through the microfluidizer at 10,000 psi. the particle size was 62 nm (0.27 chi squared, 0.47 coefficient of variance). About 2–3 hours after microfluidization, one half of the particulate suspension was passed through a Sephadex 10(S-10) desalting column to remove base, salts, and excess ligand. The remaining particulate suspension was retained as a control. Following S-10 purification, the particle size was 78 nm (3.3 chi squared, 0.44 coefficient of variance). Six days later, the particle size of the S-10 purified sample was 100 nm (0.40 chi squared, 0.38 coefficient of variance). After 12 days, the size of the particles that were passed through the microfluidizer but were not purified and stored in the base solution increased to 744 nm (4.22 chi squared, 0.57 coefficient of variance). In contrast, after 12 days the S-10 purified fraction had a particle size of 77 nm (0.65 chi squared, 0.44 coefficient of variance).

EXAMPLE 7

Preparation of Hydroxyapatite Particles Doped with Mn, Coated with ATMP, Passed through Microfluidizer, and Purified Manganese containing hydroxyapatite particles were prepared according to the procedure of Example 1, except that the particles were not coated with HEDP and were not purified by centrifuging, decanting, and washing, but left in the base and salt solution. An ATMP solution was prepared by mixing 0.0027 moles or 1.6 mL of a 50% aqueous solution with 25 mL D.I. $H_2O$ and degassing for 30 minutes under argon. The ATMP solution was added dropwise to the particles. The particle size before passing through a microfluidizer was 1465 nm and difficult to analyze due to settling. After passing the particulate suspension through the microfluidizer at 10,000 psi the particle size was 85 nm (0.58 chi squared, 0.41 coefficient of variance). The particulate suspension was divided into two parts. One part was passed through a Sephadex 10 ( S-10 ) desalting column to remove base, salts, and excess ligand. The remaining part of the particulate suspension was retained as a control. Following S-10 purification, the particle size was 67 nm ( 0.25 chi squared, 0.44 coefficient of variance). Six days later, the particle size of the S-10 purified sample was 131 nm (0.60 chi squared, 0.39 coefficient of variance). There were three populations in the S-10 fraction: 66 nm (45%), 193 nm (38%) and 665 nm (16%). After 12 days, the fraction that was stored in base solution had a particle size of 515 nm (0.50 chi squared, 0.47 coefficient of variance).

From the foregoing Examples, it appears the apatite particles are stabilized better with removal of the base, salts, and excess phosphonate. The particles tend to grow at a fast rate when stored in the reaction solution, but growth of purified particles is either stopped or inhibited. There seems to be a preference for the formation of smaller particles when the microfluidizer experiments are carried out in the base rather than the washed particles.

EXAMPLE 8

Preparation of Hydroxyapatite Particles Doped with Mn, Coated with HEDP, Passed through Microfluidizer, and Purified by Tangential Flow Filtration Manganese containing hydroxyapatite particles were prepared by the following general procedure. A procedure is described for particles containing 10% Mn but other percentages are also applicable.

Into a 1 L erlenmeyer flask were placed 10.55 g of $(NH_4)_2HPO_4$, 100 mL of concentrated $NH_4OH$ and 300 mL of D.I. water. The mixture was stirred for one hour with a continuous heavy argon flow (degassing). In a separate 1 L erlenmeyer flask were placed 28.9 g of $Ca(NO_3)_2 \cdot 4H_2O$ and 2.42 g (0.01355 moles) of $Mn(NO_3)_2 \cdot 6H_2O$ in 200 mL of D.I. water. The metal nitrate solution was degassed with argon for one hour. The phosphate solution was then added dropwise to the rapidly stirred metal nitrate mixture over 15 minutes with a peristaltic pump. A continuous argon flow was maintained throughout the course of the reaction. The reaction mixture was stirred for an additional one hour after the addition was complete. A solution of 5 g or 8.3 mL of a 60% solution HEDP (acid form) in 20 mL of D.I. water was degassed for 30 minutes then added dropwise to the hydroxyapatite mixture. The resulting slurry was stirred for 1.5 hours.

Two thirds of the reaction mixture was passed through a microfluidizer at 10,000 psi. The particle size before passing through a microfluidizer was 800 nm (27 chi squared, 0.92 coefficient of variance). After passing the particulate suspension through the microfluidizer, the particle size was 53 nm (2.2 chi squared, 0.48 coefficient of variance). The particulate suspension was then purified to remove base, salts, and excess ligand by passing it through a tangential flow filtration (sometimes referred to as "ultrafiltration") system. The tangential flow filtration system was obtained from Koch Membrane Systems, Inc., Wilmington, Mass. After each filtration pass,, the osmolality was measured. A total of 10 filtration passes were made followed by a 3-fold concentration step.

Following filtration, the particle size was 67 nm (0.43 chi squared, 0.44 coefficient of variance). After 12 days, the size of the particles that were passed through the microfluidizer but were not purified and stored in the base solution increased to 744 nm (4.22 chi squared, 0.57 coefficient of variance). In contrast, after 12 days the filtered fraction had a particle size of 82 nm (2.7 chi squared, 0.41 coefficient of variance).

Figure 2:
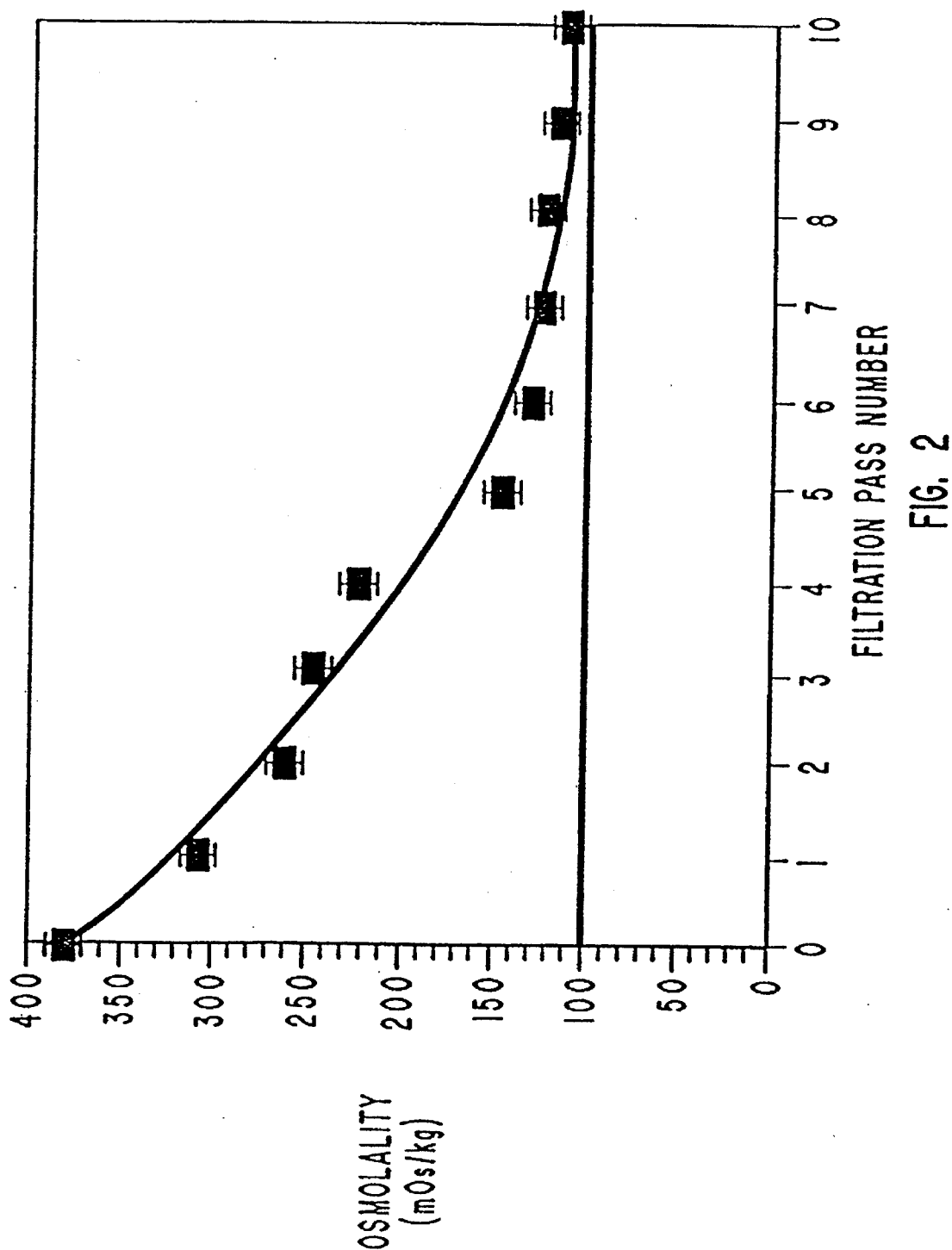
FIG. 2 is a graphical representation of the osmolality of a particulate suspension after sequential passes through a tangential flow filtration system as described in Example 8.

The results of this Example are illustrated graphically in FIGS. 1 and 2.

EXAMPLE 9

Preparation at 100° C. of Hydroxyapatite Particles Modified by Surface-Adsorbed Mn, Coating with HEDP, Passage through Microfluidizer, and Purification Calcium hydroxyapatite particles are prepared by the following procedure:

A solution containing 6.5 g of $(NH_4)_2HPO_4$ in 120 mL of D.I. water is treated with 60 mL of concentrated $NH_4OH$ followed by 90 mL of D.I. water. The resulting solution is stirred for 3 hours at room temperature.

Into a 3-neck 1 L round bottom flask equipped with a water cooled and low temperature condenser sequence (dry ice/isopropanol), mechanical stirrer and rubber septum are placed 19.4 g of $Ca(NO_3)_2 \cdot 4H_2O$ in 468 mL of D.I. water. The solution is heated to reflux. The phosphate mixture is added to the rapidly stirred calcium nitrate solution dropwise with a peristaltic pump over one hour. The heat is removed when the addition is complete and the reaction mixture is cooled to room temperature. The hydroxylapatite slurry is stirred overnight at room temperature.

The pH of the reaction mixture is decreased from 9.53 to 8.50 with 169 ml of 1 N HCl. Manganese nitrate, $Mn(NO_3)_2 \cdot 6H_2O$ (2.10 g) is added to the hydroxyapatite mixture and stirred for 1 hour and 15 minutes. The color of the slurry is pale tan. The mixture is passed through a tangential flow filter to remove excess manganese nitrate from the apatite particles. The particulate slurry is then treated with 0.54 M HEDP (Ca/HEDP mole ratio=1.2) and stirred for 1.5 hours. The color of the mixture is pale pink/purple.

The HEDP treated hydroxyapatite particulate suspension is passed through a microfluidizer at a pressure of 5000 psi. The particulate suspension is then purified to remove base, salts, and excess ligand by passing it through a tangential flow filtration system.

EXAMPLE 10

Preparation of Mn-Doped Hydroxyapatite Particles Having a Functionalized Coating Agent, Passage Through Microfluidizer and Purification by Filtration This example describes the general preparation of hydroxyapatite particles having a functionalized coating agent where the functionalized coating agent is defined as one with the ability to bind tightly to the particles and contains a pendant group to which other organic biomolecules or organic may be attached. The particles are prepared by adding 0.1 to 100 mole % of an appropriate coating agent to a slurry of Mn(II) substituted hydroxyapatite with 0.1 to 100 mole % Mn based on the Ca used in the reaction. The mixture is stirred from 1 to 360 minutes at temperatures in the range from 4° C. to 100° C. The particulate suspension is passed through a microfluidizer at a pressure in the range from 2000 to 20,000 psi, and the solid separated from the supernatant and purified from excess ions and coating agent by tangential flow filtration. The solid may be treated with a metal salt (0.01 to 10 mole % based on the total metal in the preparation). This is especially appropriate if the coating agent contains a pendant chelating group designed to capture and hold tightly the metal when subjected to in vitro and/or in vivo solutions. The resultant solid is purified to remove loosely attached coating agent or free metal/coating agent complex by tangential flow filtration.

EXAMPLE 11

Preparation of Hydroxyapatite Particles by treating with Diethylenetriamine-penta(methylenephosphonic acid), Surface Adsorbing Mn, Passing through Microfluidizer, and Purification Calcium hydroxyapatite is prepared by the following procedure and treated with the polyphosphonate, diethylenetriaminepenta(methylenephosphonic acid) (abbreviated DETAPMDP) having the following formula:

A basic ammonium phosphate solution is prepared using 6.34 g of $(NH_4)_2HPO_4$ in 120 mL of D.I. water. Concentrated ammonium hydroxide (60 mL) is added followed by 90 ml of D.I. water. The mixture is stirred for 4 hours at room temperature.

A solution of 19.0 g of $Ca(NO_3)_2 \cdot 4H_2O$ in 468 mL of D.I. water is placed in a 3-neck 1 L round bottom flask. The reaction setup includes a mechanical stirrer, water cooled and low temperature (dry ice/isopropanol) condenser arrangement, and a rubber septum. The solution is heated to reflux with rapid stirring. The basic phosphate solution is added dropwise with a peristaltic pump over one hour. The heat is removed after the addition is complete and the reaction mixture stirred overnight at room temperature.

The hydroxyapatite slurry is treated with a solution of DETAPMDP (Ca/DETAPMDP mole ratio=1.1, pH of DETAPMDP 6.3 ) and stirred at room temperature for 2.5 hours. The phosphonate treated mixture is then reacted with $Mn(NO_3)_2 \cdot 6H_2O$ (Ca/Mn mole ratio=2.3 ) and stirred for an additional 3.5 hours. The reaction mixture is passed through a microfluidizer at a pressure of 5000 psi and purified by tangential flow filtration.

From the foregoing, it will be appreciated that the present invention provides an improved method for preparing solid calcium phosphate-containing particles for medical diagnostic applications having a controlled particle size distribution and good yield.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of preparing a calcium/oxyanion-containing particle for use in medical diagnostic imaging of body organs and tissues comprising the steps of:

(a) obtaining calcium/oxyanion-containing particles having the following general formula:

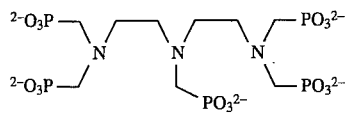

wherein M is radioactive metal ion or stoichiometric mixture of metal ions, X is a simple anion, Y is an oxyanion, tetrahedral oxyanion, protonated or unprotonated, carbonate, or mixtures thereof, n is from 1 to 10, m is from 0 to 10, s is $\geq 1$, and r is adjusted as needed to provide charge neutrality; and (b) passing the calcium/oxyanion-containing particles through a microfluidizer.

2. A method of preparing a calcium/oxyanion-containing particle for use in medical diagnostic imaging as defined in claim 1, wherein the particles passed through the microfluidizer have a particle size in the range from about 5 nm to about 5 μm and are used for imaging the liver and spleen.

3. A method of preparing a calcium/oxyanion-containing particle for use in medical diagnostic imaging as defined in claim 1, wherein the particles passed through the microfluidizer have a particle size in the range from about 1 nm to about 50 nm and are used for imaging the blood pool.

4. A method of preparing a calcium/oxyanion-containing particle for use in medical diagnostic imaging as defined in claim 1, further comprising the step of coating the particles with a coating agent to stabilize the calcium/oxyanion-containing particles.

5. A method of preparing a calcium/oxyanion-containing particle for use in medical diagnostic imaging as defined in claim 4, wherein the coating agent is selected from aminophosphonates, biomolecules, and compounds containing one or more phosphonate, carboxylate, phosphate, sulfate, or sulfonate moiety.

6. A method of preparing a calcium/oxyanion-containing particle for use in medical diagnostic imaging as defined in claim 4, wherein the coating agent contains one or more phosphonate moieties.

7. A method of preparing a calcium/oxyanion-containing particle for use in medical diagnostic imaging as defined in claim 4, wherein the coating agent is 1-hydroxyethane-1,1-diphosphonic acid and physiologically compatible salts thereof.

8. A method of preparing a calcium/oxyanion-containing particle for use in medical diagnostic imaging as defined in claim 4, wherein the coating agent contains a reactive functional group.

9. A method of preparing a calcium/oxyanion-containing particle for use in medical diagnostic imaging as defined in claim 8, wherein the reactive functional group is an amine, active ester, alcohol, or carboxylate functional group.

10. A method of preparing a calcium/oxyanion-containing particle for use in medical diagnostic imaging as defined in claim 8, wherein the reactive functional group is capable of chelating a metal ion.

11. A method of preparing a calcium/oxyanion-containing particle for use in medical diagnostic imaging as defined in claim 4, wherein the step of coating the particles with a coating agent is performed after the step of passing the particles through a microfluidizer.

12. A method of preparing a calcium/oxyanion-containing particle for use in medical diagnostic imaging as defined in claims 4, wherein the step of coating the particles with a coating agent is performed during the step of passing the particles through a microfluidizer.

13. A method of preparing a calcium/oxyanion-containing particle for use in medical diagnostic imaging as defined in claim 4, wherein the step of coating the particles with a coating agent is performed before the step of passing the particles through a microfluidizer.

14. A method of preparing a calcium/oxyanion-containing particle for use in medical diagnostic imaging as defined in claim 1, further comprising the step of purifying the calcium/oxyanion-containing particles from base and salts used to synthesize the calcium/oxyanion-containing particles.

15. A method of preparing a calcium/oxyanion-containing particle for use in medical diagnostic imaging as defined in claim 14, wherein the calcium/oxyanion-containing particles are purified by filtration.

16. A method of preparing a calcium/oxyanion-containing particle for use in medical diagnostic imaging as defined in claim 14, wherein the calcium/oxyanion-containing particles are purified by tangential flow filtration.

17. A method of preparing a calcium/oxyanion-containing particle for use in medical diagnostic imaging as defined in claim 14, wherein the calcium/oxyanion-containing particles are purified by passage through a desalting column.

18. A method of preparing a calcium/oxyanion-containing particle for use in medical diagnostic imaging as defined in claim 14, wherein the step of purifying the calcium/oxyanion-containing particles is performed after the step of passing the particles through a microfluidizer.

19. A method of preparing a calcium/oxyanion-containing particle for use in medical diagnostic imaging as defined in claim 14, wherein the step of purifying the calcium/oxyanion-containing particles is performed before the step of passing the particles through a microfluidizer.

20. A method of preparing a calcium/oxyanion-containing particle for use in medical diagnostic imaging as defined in claim 1, wherein the step of obtaining the calcium/oxyanion-containing particles is performed by passing reaction streams containing base and salts required to synthesize the calcium/oxyanion-containing particles through a microfluidizer.

* * * * *